(12) United States Patent
Cieślik et al.

(10) Patent No.: US 8,303,971 B2  
(45) Date of Patent: Nov. 6, 2012

(54) PREPARATION FOR REGENERATION OF POSTOPERATIVE, POST-TRAUMATIC BONE DEFECTS AND METHOD FOR IMPLANTATION OF THIS PREPARATION

(76) Inventors: Tadeusz Cieślik, Zabrze (PL); Jacek Nocoń, Erkrath (DE); Jan Rauch, Wadowice (PL)

(*) Notice: Subject to any disclaimer, the term of this patent is extended or adjusted under 35 U.S.C. 154(b) by 599 days.

(21) Appl. No.: 12/321,280

(22) Filed: Jan. 20, 2009

(65) Prior Publication Data

US 2009/0186063 A1 Jul. 23, 2009

(30) Foreign Application Priority Data

Jan. 17, 2008 (EP) ..................... 08460001

(51) Int. Cl.
*A61F 2/00* (2006.01)

(52) U.S. Cl. .................. 424/422; 424/423

(58) Field of Classification Search .......... None
See application file for complete search history.

(56) References Cited

U.S. PATENT DOCUMENTS

| | | | | |
|---|---|---|---|---|
| 4,728,570 A | * | 3/1988 | Ashman et al. | 428/327 |
| 4,917,702 A | * | 4/1990 | Scheicher et al. | 424/423 |
| 6,235,225 B1 | | 5/2001 | Okada et al. | |
| 6,326,018 B1 | * | 12/2001 | Gertzman et al. | 424/423 |
| 2002/0064516 A1 | * | 5/2002 | Arvinte et al. | 424/85.1 |

FOREIGN PATENT DOCUMENTS

| | | |
|---|---|---|
| EP | 0577342 | 1/1994 |
| WO | 9840113 | 9/1998 |

OTHER PUBLICATIONS

XP 009025391, vol. 22, Jan. 1, 1986—p. 328/329. Hanker J S:et al: Setting of Composite Hydroxylapatite/Plaster Implants With Blood for Bone Reconstruction.

XP 000869797, Jan. 1,1995, pp. 17-24, Bergman S A et al: "Bone In-Fill of Non-Healing Calvarial Defects Using Particulate Bioglass and Autogenous Bone Bioceramis".

* cited by examiner

*Primary Examiner* — Elizabeth C Kemmerer
(74) *Attorney, Agent, or Firm* — Horst M. Kasper

(57) ABSTRACT

According to the invention preparation for regeneration of bone defects is employed in many branches of medicine, especially in orthopedics, dental surgery, reconstructive surgery, periodonthology and implantology. The preparation has been developed on the basis of inorganic chemical compound naturally occurring, i.e. deproteinized human bone, and on the basis of at least one of inorganic chemical compounds synthetically occurring, i.e. bioglass in the form of granulated high calcium product (54% mol. CaO), obtained with the use of zol-gel method in the system $CaO$—$SiO_2$—$P_2O_5$, of density 2.9082 $g/cm^3$, with phase composition with a dominant glassy phase and beginnings of crystallization of apatite, heat treated at temperature of 800° C., having a specific surface BET 57.8166 $m^2/g$ and/or tricalcium phosphate—TCP in the form of granulated product with chemical formula $Ca_3(PO_4)_2$. As a component deproteinized particles of human bone are used, favorably with granulation 0.3-0.5 mm, bioglass favorably with granulation 0.3-0.5 mm and/or TCP—tricalcium phosphate favorably with granulation 0.3-0.5 mm. The amount of bone material in the preparation amounts favorably to 70-80% of the preparation weight, the amount of bioglass in preparation amounts favorably to 10-15% of the preparation weight, the amount of TCP in the preparation amounts favorably to 10-15% of the preparation weight. During implantation binder in the form of blood from patient's operative wound is introduced into the preparation. Amount of the preparation in mixture favorably amounts to 75-80% of the mixture weight and the amount of own blood favorably amounts to 20-25% of the mixture weight.

10 Claims, No Drawings

PREPARATION FOR REGENERATION OF POSTOPERATIVE, POST-TRAUMATIC BONE DEFECTS AND METHOD FOR IMPLANTATION OF THIS PREPARATION

The subject of the invention is a preparation for regeneration of postoperative and post-traumatic bone defects and method for implantation of this preparation, employed in many branches of medicine especially in orthopedics, dental surgery, reconstructive surgery, periodenthology and implantology.

Nowadays popularly applied xenogeneic grafts or implants e.g. compositions of horse bone and cattle bone create a risk of transmission of animal diseases, e.g. BSE (Bovine Spongiform Encephalopathy). There is also a potential risk of transmission of pathogenic micro-organisms.

There are also autogenic bone implants of patient's own bone, most often taken from oral cavity area. Bone can also be collected from other patient's anatomic areas, but it cannot be done in a dentist's office. Most often such surgery is performed in a clinic.

The objective of this invention is creating a new therapeutically effective preparation for regeneration bone defects, which will show low biotoxicity and small systematic side effects at surgical application.

This invention helps to fulfill the above task. For purposes of clarity the preparation components have been marked with letters A, B, C, TCP. The essence of this preparation is application of a deproteinized human bone (A), deprived of the smallest molecules of protein, with granulation from 0.3 to 0.5 mm, bioglass (B) with granulation from 0.3 to 0.5 mm and binder (C) favorably in the form of a patient's own blood in the amount of 20-25% in relation to the quantitative sum of the above components. The deproteinized human bone can have a contents of protein of less than 500 nanograms per microliter after the deproteinazation and preferably of less than 100 nanograms per microliter after the deproteinazation. For making this preparation one could use human bone (A) available in tissue bank in the form of hydroxyapatite, with appropriate granulation, as well as in the form of trochlea. The second component of the preparation bioglass (B), in the form of powder with granulation 0.3-0.5 mm, can be obtained with use of zol-gel method in the system $CaO-SiO_2-P_2O_5$. This component can also be used as a high silica component (80% mol. $SiO_2$) or/and as a high calcium component (54% mol. CaO). High silica component of a density 2.4037 $g/cm^3$, heat treated at temperature of 700° C., amorphous, has a specific surface BET 297.9663 $m^2/g$. Whereas high calcium component of a density 2.9082 $g/cm^3$, with phase composition with a dominant glassy phase and beginnings of crystallization of apatite, heat treated at temperature of 800° C., has a specific surface BET 57.8166 $m^2/g$. This kind of bioactive glass of preparation spontaneously forms union with maternity tissue and stimulates regeneration of bone tissue. Under "in vivo" conditions on the surface of biomaterial hydroxy apatite layer (HAp) crystallizes with chemical and mineralogical composition similar to bone HAp (natural). In this way an exceptionally durable chemical bond (bonding interface) is formed. In a living organism in the presence of bioglass numerous biochemical and biological processes take place, e.g. protein adsorption, synchronized cells occurrences which result in a quick forming of administered bone tissue. The invention also anticipates that instead of bioglass (B), a tricalcium phosphate (TCP) could be applied—favorably with granulation 0.3-0.5 mm, in the amount of 15-20% of the preparation weight. A bioglass (B) and/or tricalcium phosphate TCP is designated in the context of this application as a glassy material.

Unexpectedly it has also turned out that it in possible to get very good therapeutic results in regeneration of bone defects, by compiling all the above mentioned components of the preparation. As components are simultaneously used deproteinized preparation of bone (A) with granulation 0.3-0.5 mm in the amount favorably 70-80% of the preparation weight, bioglass (B) in the form of granulated product in the amount favorably 10-15% of the preparation weight, tricalcium phosphate TCP favorably 10-15% of the preparation weight, and binder (C) favorably in the amount of 20-25% of the preparation weight in relation to the quantitative sum of the amount of the above components. Alternatively, as components can be simultaneously used deproteinized preparation of bone (A) with granulation 0.3-0.5 mm in the amount favorably 70-80% of the preparation weight, a member selected from the group consisting of bioglass (B) in the form of granulated product, tricalcium phosphate TCP, and mixtures thereof in the amount favorably 10-15% of the preparation weight, and binder (C) favorably in the amount of 20-25% of the preparation weight in relation to the quantitative sum of the amount of the above components.

Particular components are mixed in strictly defined proportions and strictly defined granulation. There are several reasons why it should be done this way. The main reason is atrophy of bone structure during spontaneous healing of wounds that reaches 20-30% of volume. Application of deproteinized human bone supplements natural hydroxy apatite in a wound, TCP slows down the process of atrophy and in this way reduces biodegradation, whereas bioglass due to its biologically active surface stimulates osteogenesis and functions as space filler when not being subjected to biodegradation.

This invention enables a faster regeneration of human bone tissue defects arising from intended activities, such as surgical activities, or unintended activities—injuries and disease process. Application of the above preparation results in a fast and complete regeneration of anatomic profile and physiological function. This invention helps to speed up the process of regeneration of damaged bone, and it contributes to compensation of biodegradation during the process of healing, due to active surfaces of the applied filler.

According to this invention an appropriate amount of the preparation is being mixed with binder i.e. the blood from operative wound (the mixture should be homogeneous). The obtained mixture which has consistency of Plasticine, is implanted into bone defects. Application of a patient's own blood enriches the implanted preparation with organic components, e.g. collagen type 1, proteins, polysaccharides, lipids, necessary for osteogenesis and for preventing the preparation components from moving inside the operative wound. The components contained in a regenerating bone amount to 25% of the bone's weight. The components enumerated above, especially collagen, increase bone's resistance to mechanical destruction caused by tension that occurs during work, and reduce brittleness of bones. Moreover collagen and protein fibers accelerate crystallization of hydroxyapatite.

The invention claimed is:

1. A preparation for regenerating bones wherein said preparation comprises a granular component and 20 to 25 percent by weight blood as a binder, wherein the granular component comprises granulated deproteinized human bone (A) having a particle size in the range 0.3 to 0.5 mm, and a granulated glassy material(B) according to formulation (1) or (2), wherein formulation (1) comprises 80 to 85 percent by weight component (A) and 15 to 20 percent by weight component (B), wherein component (B) comprises bioglass or tricalcium phosphate and the percent by weight amounts are based on the total weight of formulation (1), and formulation (2) comprises 70 to 80 percent by weight component (A), 10 to 15 percent by weight bioglass, and 10 to 15 percent by weight tricalcium phosphate, wherein the percent by weight amounts are based on the total weight of formulation (2).

2. The preparation according to the claim 1, wherein the glassy material is obtained with use of a sol-gel method in the system $CaO$—$SiO_2$—$P_2O_5$ as high silica material with 80 mol percent $SiO_2$ or as a high calcium material with 54 mol percent CaO.

3. The preparation according to the claim 1, wherein a patient's own blood is used as the binder.

4. The preparation according to the claim 1, wherein the glassy material is tricalcium phosphate and wherein the tricalcium phosphate has a particle size in the range from 0.3-to 0.5 mm.

5. A method of implantation comprising;
   mixing blood from an operative wound with granular componets comprising granulated deproteinized human bone (A) having a panicle size in the range from 0.3 to 0.5 mm and a granulated glassy material (B), wherein the granular components comprise 80 to 85 percent by weight component (A) and 15 to 20 percent by weight component (B), wherein the percent by weight amounts are based on the total weight of the granular components, until the mixture contains 20 to 25 percent by weight blood and the mixture becomes homogenous; and
   implanting the obtained mixture into bone defects.

6. The method of claim 5, wherein said glassy material is a $CaO$—$SiO_2$—$P_2O_5$ bioglass, wherein the bioglass has a high silica content of up to 80 mol percent $SiO_2$ or high calcium content of up to 54 mol percent CaO.

7. The method of claim 5, wherein the glassy material is granulated tricalcium phosphate (TCP) particles that are 0.3 to 0.5 mm in diameter.

8. A method of regenerating bone to repair post-operative or post-traumatic bone defects, comprising:
   mixing a preparation comprising (A) deproteinized, granulated human bone particles having a diameter of 0.3 to 0.5 mm, (B) granulated glassy material, and (C) blood obtained from the patient during surgery as a binder to form a homogeneous putty, and implanting said preparation at the site of a bone defect, wherein the granular components comprise 80 to 85 percent by weight component (A) and 15 to 20 percent by weight component (B), based on the total weight of the granular components, and the blood comprises 20 to 25 percent by weight based on the total weight of the preparation.

9. The method according to claim 8, wherein said glassy material is a $CaO$—$SiO_2$—$P_2O_5$ bioglass, a high silica content of up to 80 mol percent $SiO_2$ or high calcium content of up to 54 mol percent CaO.

10. The method according to claim 8, wherein the glassy material is granulated tricalcium phosphate (TCP) particles that are 0.3 to 0.5 mm in diameter.

* * * * *